United States Patent [19]

Kung et al.

[11] Patent Number: 4,672,108

[45] Date of Patent: Jun. 9, 1987

[54] CRYSTALLINE HUMAN LEUKOCYTE INTERFERON

[75] Inventors: Hsiang-Fu Kung, Verona; David L. Miller, Montclair; Sidney Pestka, North Caldwell, all of N.J.

[73] Assignee: Hoffmann-La Roche Inc., Nutley, N.J.

[21] Appl. No.: 751,754

[22] Filed: Jul. 3, 1985

Related U.S. Application Data

[63] Continuation of Ser. No. 655,302, Sep. 26, 1984, abandoned, which is a continuation of Ser. No. 538,850, Oct. 6, 1983, abandoned, which is a continuation of Ser. No. 327,876, Dec. 7, 1981, abandoned.

[51] Int. Cl.⁴ .................... C07K 15/26; A61K 45/02; C12P 21/00
[52] U.S. Cl. .................... 530/351; 424/85; 435/811
[58] Field of Search ...... 424/85; 260/112 R, 112.5 R; 530/351; 435/68, 811

[56] References Cited

U.S. PATENT DOCUMENTS

| | | | |
|---|---|---|---|
| 4,177,188 | 12/1979 | Hansen | 424/101 |
| 4,197,238 | 4/1980 | Murata et al. | 424/101 |
| 4,289,690 | 9/1981 | Pestka et al. | 424/85 |

OTHER PUBLICATIONS

Nagata, S., et al., Nature, vol. 284, pp. 316–320, 1980.
Rubenstein, M., et al., Proc. Natl. Acad. Sci., vol. 76, pp. 640–644, 1979.
McPherson, Jr., A., J. Biol. Chem., vol. 251, pp. 6300–6303, 1976.
Goeddel et al., Nature, vol. 287, pp. 411–415, 1980.
Staehelin et al., J. Biol. Chem., vol. 256, pp. 9750–9754, 1981.

*Primary Examiner*—Blondel Hazel
*Attorney, Agent, or Firm*—Jon S. Saxe; George M. Gould; Norman C. Dulak

[57] ABSTRACT

The crystallization of human leukocyte interferon is described. In a preferred embodiment crystalline recombinant human leukocyte interferon A (IFL-rA) is prepared.

1 Claim, No Drawings

CRYSTALLINE HUMAN LEUKOCYTE INTERFERON

This is a continuation of application Ser. No. 655,302 filed Sept. 26, 1984 now abandoned, which is a continuation of Ser. No. 538,850 filed Oct. 6, 1983 now abandoned, which is a continuation of Ser. No. 327,876 filed Dec. 7, 1981, now abandoned.

BACKGROUND

Human leukocyte interferons designated $\alpha_1$, $\alpha_2$, $\beta_1$, $\beta_2$, $\beta_3$, $\gamma_1$, $\gamma_2$, $\gamma_3$, $\gamma_4$, and $\gamma_5$ derived from virus induced normal or leukemic donors' leukocytes have been purified to homogeneity, see U.S. Pat. No. 4,289,690, issued Sept. 15, 1981. More recently, recombinant DNA technology has been employed to occasion the microbial production of a number of different leukocyte interferons amino acid sequences exhibit on the order of 70 percent or more homology, one relative to another as disclosed in U.S. Patent Application Ser. No. 205,578, filed Nov. 10, 1980, now abandoned, Inventors Goeddel and Pestka. Specific recombinant human leukocytes described in this application are IFL-rA, B, C, D, F, G, H, I and J. Additionally, U.S. Patent Application Ser. No. 305,657, filed Sept. 25, 1981, now U.S. Pat. No. 4,456,748, Inventor, Goeddel, describes the microbial production via recombinant DNA techology of hybrid leukocyte interferons. Examples of such hybrid leukocyte interferons include IFLr $A_{1-91}D_{93-166}$, $D_{1-92}A_{92-165}$, $A_{1-62}D_{64-166}$ $D_{1-63}A_{63-165}$, $A_{1-91}B_{93-166}$, $A_{1-91}F_{93-166}$, $A_{1-91}G_{93-166}$, $A_{1-150}I_{151-165}$, $B_{1-92}A_{92-165}$ $B_{1-92}D_{93-166}$, $B_{1-92}F_{93-166}$, $B_{1-92}G_{33-166}$, $D_{1-92}B_{93-166}$, $D_{1-92}F_{93-166}$, $D_{1-92}G_{93-166}$, $F_{1-92}A_{92-165}$, $F_{1-92}B_{93-166}$, $F_{1-92}D_{93-166}$, $F_{1-92}G_{93-166}$, and $I_{1-151}A_{152-166}$.

The aforesaid natural, recombinant and hybrid human leukocyte interferons represent a family of proteins characterized by a potent ability to confer a virus-resistant state in their target cells. In addition, these interferons can act to inhibit cell proliferation and modulate immune response. These properties have prompted the initial clinical use of IFLrA and IFLrD as therapeutic agents for the treatment of viral infections and malignancies.

Crystallization of a substance satisfies one of the classical criteria for homogeneity. Additionally, the crystallization process itself can provide a useful purification step. The availability of large ordered crystals of human leukocyte interferons will also allow the determination of the molecule's tertiary structure utilizing X-ray crystallization.

Numerous techniques have been developed for the crystallization of proteins, however, no generalized procedure has been discovered, and many proteins remain uncrystallized. Thus, crystallization of proteins is an unpredictable art utilizing trial and error procedures among many possible alternative methodologies.

One of the most widely used approach involves the addition to the protein solution of a crystallizing agent, which is commonly a salt, such as ammonium sulfate or ammonium citrate or an organic solvent, such as ethanol or 2-ethyl-2, 4-pentanediol. However, such procedures do not provide a suitable means for producing crystalline human leukocyte interferons.

A versatile crystallizing agent is polyethylene glycol (PEG), which combines some of the characteristics of the salts and the organic solvents. See in this regard K. B. Ward et al., J. Mol. Biol. 98, 161(1975) and A. McPherson, Jr., J. Biol. Chem. 251, 6300 (1976). It has now been discovered that polyethylene glycol and particularly polyethylene glycol 4000 can be successfully used to crystallize the aforementioned human leuckocyte interferons, most particularly IFL-rA.

The human leukocyte interferons employed as starting materials in the instant crystallization process can be isolated by procedures providing the compounds in an essentially homogeneous state. Such procedures include high performance liquid chromatography (HPLC) such as described in the aforesaid U.S. Pat. No. 4,289,690, affinity chromatography utilizing a monoclonal antibody to human leukocyte interferon supported on a column support material as described, for example, by T. Staehelin et al., J. Biol. Chem. 256, 9750–9754 (1981) or any other procedure providing human interferon in sufficient purity ($>95\%$) and in sufficient concentration ($\geq 0.2$ mg/ml interferon).

There are a number of important advantages attending to being able to obtain human leukocyte interferons in crystalline form. As indicated above one evident advantage is the additional purification available from crystallization step which could remove different impurities than the HPLC or conventional column chromatography can achieve. Moreover, crystalline human leukocyte can be stored and shipped at ambient temperatures free of the risk of protease contamination possible in solution storage. Other techniques for producing proteins such as lyophilization are known to cause some denaturation of interferon as evidenced by a loss in the value of the specific activity of samples before and after such procedures.

A suitable procedure for the crystallization of one of the human leukocyte interferons, IFL-rA, is set forth below in the Example. In analogous fashion the other human leukocyte interferons which exhibit a high degree of sequence homology can be crystallized.

EXAMPLE

Materials

Recombinant human leukocyte interferon A(IFLrA)
Polyethylene glycol 4000
N-2-Hydroxyethylpiperazine-N'-2-ethane sulfonic acid (HEPES)
Sodium azide
Dimethyldichlorosilane
Nine-well glass spot plate

Procedure

IFLrA (4 ml, 0.2 mg/ml) was dialyzed overnight at 4° against 0.01 M HEPES, adjusted to pH 7.1 with NH$_4$OH. The solution was concentrated fivefold by certrifugal evaporation (Speed-Vac, Virtis), redialyzed against 0.01 M HEPES (pH 7.1), and further concentrated to 5 mg/ml. The final concentration was determined by ultraviolet spectrophotometry.

The spot plate was siliconized prior to use by dipping it in 5% (v/v) dimethyldichlorosilane in carbon tetrachloride, and then baking it at 180°. It was washed with water and rebaked. In each of four wells, 20 $\mu$l of the interferon solution was placed. A PEG solution (200 mg/ml) containing NaN$_3$ (0.5 mg/ml) was added to each well to give final concentrations of 20, 40, 60, and 100 mg/ml. The droplets were immediately mixed using a micropipettor, and the spot plate was placed above a solution of 100 mg/ml PEG contained in a crystallizing dish. The dish was sealed and kept at 4°. After 1–3 days, crystals appeared in each of the wells. After several more days, larger crystals appeared in some of the droplets.

The crystals were separated from the liquid phases by centrifugation, washed with 0.05 M HEPES (pH 7.1) containing 10% PEG, and redissolved in 0.05 M HEPES, pH 7.1. Bioassays of the solutions prepared from the 10% PEG mixture revealed that the crystals contained interferon activity. Most of the interferon activity (>90%) was recovered in the crystals. The crystallized protein was indistinguishable from the uncrystallized IFLrA by gel electrophoresis, which confirms that the crystalline product is uncleaved and intact.

TABLE

HPLC OF PEPTIDES AND PROTEINS
RECOVERY OF INTERFERON IN CRYSTALS[a]

| | Crystals | | Supernatant | |
|---|---|---|---|---|
| Crystallization condition | Antiviral activity (units/ml) | Percentage recovery | Antiviral activity (units/ml) | Percentage recovery |
| pH 5 | $4.0 \times 10^8$ | (94) | $2.5 \times 10^7$ | (6) |
| pH 7 | $6.0 \times 10^8$ | (99) | $4.5 \times 10^8$ | (1) |
| pH 8 | $8.0 \times 10^8$ | (99) | $4.5 \times 10^8$ | (1) |

[a]The crystals were washed in 0.05 M HEPES (pH 7.1) containing 10% PEG and redissolved in 0.05 M HEPES (pH 7.1). The total antiviral activity recovered in the crystals and in the supernatant was assayed as described.[6] Values in parentheses represent the percentage recovered in the various fractions.

It is not necessary to crystallize interferon A from concentrated solutions. Microcrystals appear in solutions of 0.2 mg/ml interferon, 10% PEG. This method thus may be useful for concentrating dilute solutions of interferon. As is evident from the above Table crystallizing under slightly basic conditions i.e., about pH 8, produces crystalline IFL-rA in quantitative yield and with the highest specific activity.

We claim:

1. Human leukocyte interferon in crystalline form which is IFL-rA.

* * * * *